United States Patent [19]
Treace

[11] 3,988,783
[45] Nov. 2, 1976

[54] PROSTHETIC COLLATERAL LIGAMENT

[75] Inventor: James T. Treace, Malibu, Calif.

[73] Assignee: Richards Manufacturing Company, Inc., Memphis, Tenn.

[22] Filed: Jan. 21, 1976

[21] Appl. No.: 651,220

[52] U.S. Cl. .................................. 3/1; 3/1.911; 128/92 B; 128/92 C
[51] Int. Cl.² ........................................ A61F 1/24
[58] Field of Search .................... 3/1, 1.9–1.911; 128/92 C, 92 B, 334 R

[56] References Cited
UNITED STATES PATENTS 3,513,484   5/1970   Hausner .................................. 3/1
3,896,500   7/1975   Rambert et al. ........................ 3/1

*Primary Examiner*—Ronald L. Frinks
*Attorney, Agent, or Firm*—John R. Walker, III

[57] ABSTRACT

A prosthetic ligament for replacing one of the collateral ligaments of the knee joint. The prosthetic ligament includes a bridge member for extending across the knee joint, a first connector member for securing the first end of the bridge member to the lower end of the femur, and a second connector member for securing the second end of the bridge member to the upper end of the tibia.

9 Claims, 7 Drawing Figures

U.S. Patent  Nov. 2, 1976  3,988,783
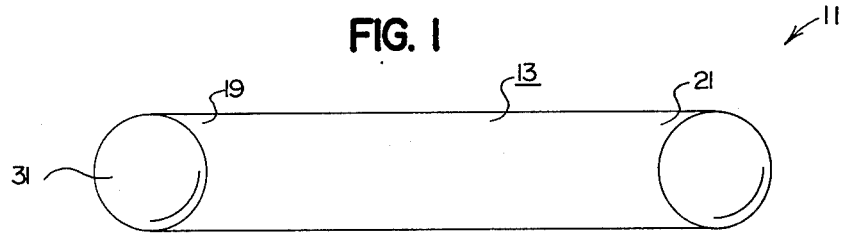
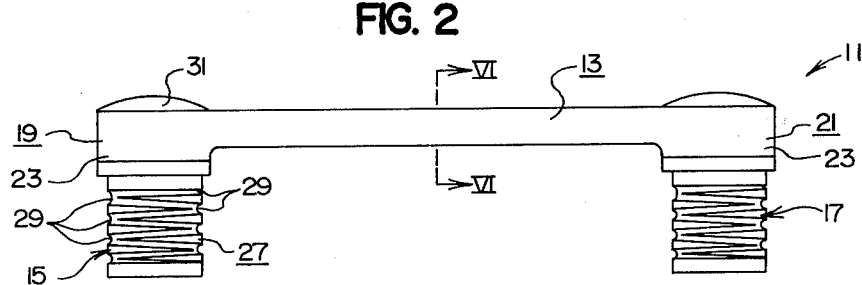
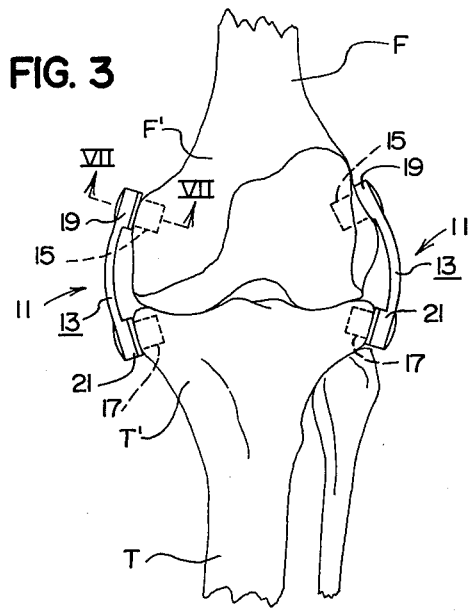
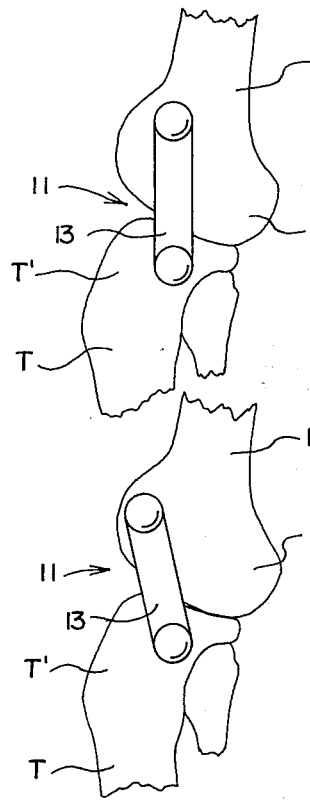
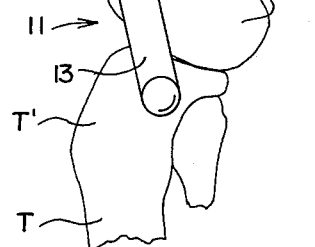
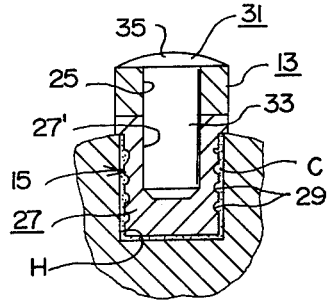

PROSTHETIC COLLATERAL LIGAMENT

BACKGROUND OF THE INVENTION

1. Field of the Invention

This invention relates in general to means for correcting defective collateral ligaments of the knee joint and more specifically to prostheses for replacing such defective collateral ligaments.

2. Description of the Prior Art

Heretofore, various means have been developed for correcting defective collateral ligaments of the knee joint. Torn or severed collateral ligaments can often be repaired by merely tying or sewing the torn or severed ends thereof back together. Similarly, loose or stretched collateral ligaments can often be corrected by gathering the excessive length of the ligament together in folds and sewing the folds together or by detaching one end of the ligament from the bone structure to which it is attached and reattaching it to the bone structure by staples or the like to a point farther away from the other end of the ligament. Often, however, such means will not permanently correct the defective ligament for one reason or another. When this happens, more drastic measures must be taken in an attempt to correct the defect. One such measure is the fusion of the knee joint together. This measure is, of course, extremely disadvantageous for a number of reasons such as the medical procedures required to do it and the resulting complete stiffness and loss of mobility. Another measure is to utilize a hinged knee device. This measure is also disadvantageous for a number of reasons such as the medical procedures required to replace the knee joint with the hinged knee device and the lack of full mobility provided by such hinged knee device. Another measure is to apply constant bracing to the knee joint. This measure is also disadvantageous for a number of reasons such as the stiffness and lack of mobility that the constant bracing causes. Another measure is to replace the collateral ligament with other body tissue such as fascia. This measure has not proved entirely satisfactory since no usable body tissue has been found to be of sufficient strength and flexibility to perform the job of the collateral ligament.

SUMMARY OF THE INVENTION

The present invention is directed towards overcoming the problems and disadvantages of the prior means for and methods of correcting defective collateral ligaments of the knee joint. The concept of the present invention is to provide a prosthesis which can be used to replace a collateral ligament of the knee joint and which gives strength and stability to the knee joint when so used while allowing substantially unhampered movement of the knee joint.

In general, the prosthesis of the present invention includes bridge means for extending across the knee joint, first connector means for securing a first end portion of the bridge means to bone structure of the lower end of the femur, and second connector means for securing a second end portion of the bridge means to bone structure of the upper end of the tibia. At least one of the connector means is pivotally attached to the bridge means.

BRIEF DESCRIPTION OF THE DRAWINGS

FIG. 1 is a plan view of the prosthetic ligament means of the present invention.

FIG. 2 is an elevational view of the prosthetic ligament means of the present invention.

FIG. 3 is a front view of a knee joint showing a prosthetic ligament means of the present invention replacing both collateral ligaments thereof.

FIG. 4 is a side view of a knee joint showing a prosthetic ligament means of the present invention replacing the fibular collateral ligament thereof.

FIG. 5 is a view substantially similar to FIG. 4 but showing an alternate position of the prosthetic ligament means of the present invention.

FIG. 6 is a sectional view of the bridge means of a prosthetic ligament means of the present invention as taken on line VI—VI of FIG. 1.

FIG. 7 is a sectional view of a prosthetic ligament means of the present invention as taken on line VII—VII of FIG. 3.

DESCRIPTION OF THE PREFERRED EMBODIMENT

A natural knee joint includes a tibial collateral ligament extending between the lower end of the femur and the upper end of the tibia on the medial side of the knee joint for giving strength and stability to the medial side of the knee joint and includes a fibular collateral ligament extending between the lower end of the femur and the upper end of the fibula on the lateral side of the knee joint for giving strength and stability to the lateral side of the knee joint. If one of these collateral ligaments becomes defective by being stretched, loosened, severed, or the like, the knee joint will become unstable and will require correction. The prosthetic ligament means 11 of the present invention is for replacing such a defective collateral ligament. In general, the prosthetic ligament means 11 of the present invention includes a bridge means 13, a first connector means 15, and a second connector means 17.

The bridge means 13 is provided for extending across the knee joint. The bridge means 13 includes a first end portion 19 for being secured to the bone structure of the lower end F' of the femur F and includes a second end portion 21 for being secured to bone structure of the upper end T' of the tibia T. Each end portion 19, 21 may be provided with a boss-like portion 23 and a transverse aperture 25 (see FIG. 7) for reasons which will hereinafter become apparent. The bridge means 13 may consist of an elongated strap-like member having a substantially rectangular cross section (see FIG. 6) and made of a somewhat flexible, biocompatible material such as ultrahigh molecular weight polyethylene or the like. The bridge means 13 is preferably substantially flexible in a backward and forward direction while being substantially nonflexible in a sideward direction. More specifically, the substantially rectangular cross section of the bridge means 13 allows the bridge means 13 to flex in a backward and forward direction (i.e., along the major axis of the rectangular cross section) while substantially preventing the bridge means 13 from flexing in a sideward direction (i.e., against the major axis of the rectangular cross section). The bridge means 13 may conveniently be provided in a plurality of different lengths for accomodating patients of different physical sizes. For example, the bridge means 13 may be conveniently provided in 3 inch (7.62 centimeters), 3.5 inch (8.89 centimeters), and 4 inch (10.16 centimeters) lengths.

The first connector means 15 is for securing the first end portion 19 of the bridge means 13 to the bone structure of the lower end F' of the femur F. The first connector means 15 may include a fixation member 27 for being fixedly attached to the bone structure of the lower end F' of the femur F. The fixation member 27 may conveniently include a plurality of transversely extending grooves 29 in the exterior surface thereof for coacting with bone cement C to fixedly secure the fixation member 27 to the bone structure of the lower end F' of the femur F. The first connector means 15 may also include a bolt-like member 31 for attaching the fixation member 27 to the first end portion 19 of the bridge means 13. The bolt-like member 31 may conveniently include a body portion 33 for passing through the aperture 25 in the first end portion 19 of the bridge means 13 and for being fixedly received in an aperture 27' in the fixation member 27 (see FIG. 7). It should be noted that the body portion 33 of the bolt-like member 31 and the fixation member 27 may be fixed relative to one another in any number of ways which should be apparent to those skilled in the art. For example, the body portion 33 of the bolt-like member 31 may be press fitted into the aperture 27' of the fixation member 27. The bolt-like member 31 may also be conveniently provided with a head portion 35 fixedly attached to the body portion 33 for causing the fixation member 27 to be secured to the first end portion 19 of the bridge means 13 (see FIG. 7). The first connector means 15 may be fixedly attached to the first end portion 19 of the bridge means 13 so that the first connector means 15 will not rotate relative to the bridge means 13. This may be accomplished in a number of ways which should be apparent to those skilled in the art. For example, glue may be applied between the first connector means 15 and the first end portion 19 of the bridge means 13 thereby causing the first connector means 19 to be fixed relative to the bridge means 13. Or, if desired, the connector means 15 and the bridge means may be integrally formed. On the other hand, the first connector means 15 may be pivotally attached to the first end portion 19 of the bridge means 13 for reasons which will hereinafter become apparent. This may also be accomplished in a number of ways which should be apparent to those skilled in the art. For example, the diameter of the body portion 33 of the bolt-like member 31 may be made smaller than the diameter of the aperture 25 through the first end portion 19 of the bridge means 13 to allow the bridge means 13 to thereby pivot relative to the first connector means 15. The fixation member 27 and the bolt-like member 31 of the first connector means 15 may be constructed of a biocompatible material such as stainless steel or the like.

The second connector means 17 is for securing the second end portion 21 of the bridge means 13 to the bone structure of the upper end T' of the tibia T. The second connector means 17 may be constructed substantially identically to the first connector means 15 and the above description of the first connector means 15 should be sufficient.

To replace a defective collateral ligament with the prosthetic ligament means 11 of the present invention, the first general step is to remove the defective collateral ligament and form a hole H in the bone structure of the lower end F' of the femur F and in the bone structure of the upper and T' of the tibia T for receiving the fixation members 27 of the first and second connector means 15, 17. It should be noted that the holes H may be formed in locations so that the prosthetic ligament means 11 may be attached to the knee joint in a position substantially aligned with the longitudinal axes of the femur F and tibia T when the knee joint is extended (see FIG. 4). On the other hand, the holes H may be formed in locations so that the prosthetic ligament means 11 may be attached to the knee joint in a position substantially misaligned with the longitudinal axes of the femur F and tibia T when the knee joint is extended (see FIG. 5) for giving the knee joint more rotational stability and the like. After the holes H have been formed, bone cement is applied thereto. Next, the prosthetic ligament means 11 is positioned across the knee joint with the fixation members 27 of the first and second connector means 15, 17 being inserted into the holes H. It should be noted that the prosthetic ligament means 11 may be used to replace one or both collateral ligaments of a knee joint (see FIG. 3). Although the invention has been described and illustrated with respect to a preferred embodiment thereof, it is not to be so limited since changes and modifications may be made therein which are within the full intended scope of the invention.

I claim:
1. Prosthetic ligament means for replacing a natural collateral ligament of the knee joint, said prosthetic ligament means comprising: bridge means for extending across the knee joint, said bridge means including a first end portion for being secured to bone structure of the lower end of the femur and including a second end portion for being secured to bone structure of the upper end of the tibia; first connector means for securing said first end portion of said bridge means to bone structure of the lower end of the femur; and second connector means for securing said second end portion of said bridge means to bone structure of the upper end of the tibia; at least one of said first and second connector means being pivotally attached to said bridge means.

2. The prosthetic ligament means of claim 1 in which both of said first and second connector means are pivotally attached to said bridge means.

3. The prosthetic ligament means of claim 2 in which said first connector means includes a fixation member for being fixedly attached to the bone structure of the lower end of the femur and includes a bolt-like member for attaching said fixation member to said first end portion of said bridge means.

4. The prosthetic ligament means of claim 3 in which said fixation member includes a plurality of transversely extending grooves in the exterior surface thereof for coacting with bone cement to fixedly secure said fixation member to the bone structure of the lower end of the femur.

5. The prosthetic ligament means of claim 2 in which said second connector means includes a fixation member for being fixedly attached to the bone structure of the upper end of the tibia and includes a bolt-like member for attaching said fixation member to said second end portion of said bridge means.

6. The prosthetic ligament means of claim 5 in which said fixation member includes a plurality of transversely extending grooves in the exterior surface thereof for coacting with bone cement to fixedly secure said fixation member to the bone structure of the upper end of the tibia.

7. The prosthetic ligament means of claim 2 in which said bridge means is substantially flexible in a backward and forward direction while being substantially non-flexible in a sideward direction.

8. Prosthetic ligament means for replacing a natural collateral ligament of the knee joint, said prosthetic ligament means comprising:
   a. bridge means for extending across the knee joint, said bridge means being formed of a biocompatible material, said bridge means including a first end portion for being secured to bone structure of the lower end of the femur and including a second end portion for being secured to bone structure of the upper end of the tibia, said bridge means being substantially flexible in a backward and forward direction and being substantially nonflexible in a sideward direction;
   b. first connector means for securing said first end portion of said bridge means to bone structure of the lower end of the femur, said first connector means including a fixation member for being fixedly attached to the bone structure of the lower end of the femur and including a bolt-like member for pivotally attaching said fixation member to said first end portion of said bridge means, said fixation member including a plurality of transversely extending grooves in the exterior surface thereof for coacting with bone cement to fixedly secure said fixation member to the bone structure of the lower end of the femur; and
   c. second connector means for securing said second end portion of said bridge means to bone structure of the upper end of the tibia, said second connector means including a fixation member for being fixedly attached to the bone structure of the upper end of the tibia and including a bolt-like member for attaching said fixation member to said second end portion of said bridge means, said fixation member including a plurality of transversely extending grooves in the exterior surface thereof for coacting with bone cement to fixedly secure said fixation member to the bone structure of the upper end of the tibia.

9. The prosthetic ligament means of claim 8 in which said bolt-like member of said second connector means is adapted to pivotally attach said fixation member of said second connector means to said second end portion of said bridge means.

* * * * *